United States Patent
Telesca et al.

(10) Patent No.: US 6,168,028 B1
(45) Date of Patent: Jan. 2, 2001

(54) PACKAGED SKIN PRODUCT

(75) Inventors: Josephine Telesca, Trumbull, CT (US); Matthew Scott Okin, Cresskill, NJ (US)

(73) Assignee: Unilever Home & Personal Care USA, division of Conopco, Inc., Greenwich, CT (US)

(*) Notice: Under 35 U.S.C. 154(b), the term of this patent shall be extended for 0 days.

(21) Appl. No.: 09/443,596

(22) Filed: Nov. 19, 1999

(51) Int. Cl.[7] .................................................. B65D 25/54
(52) U.S. Cl. ....................... 206/776; 206/439; 206/440; 206/823; 206/828; 424/449; 424/448
(58) Field of Search .................................. 424/401, 448, 424/449; 206/439

(56) References Cited

U.S. PATENT DOCUMENTS

| | | | |
|---|---|---|---|
| 4,867,146 | * | 9/1989 | Krupnick et al. ............... 128/858 |
| 5,590,778 | * | 1/1997 | Dutchik ............................ 206/439 |
| 5,636,741 | * | 6/1997 | O'Keefe ........................... 206/459.1 |
| 5,785,978 | * | 7/1998 | Porter et al. ..................... 424/401 |
| 5,860,550 | * | 1/1999 | Miller et al. .................... 220/4.23 |

FOREIGN PATENT DOCUMENTS

| | | | |
|---|---|---|---|
| 97/48387 | 12/1997 | (WO) . | |
| WO 97/48387 | * 12/1997 | (WO) ............................... A61K/9/70 |

* cited by examiner

Primary Examiner—Thurman K. Page
Assistant Examiner—Isis Ghali
(74) Attorney, Agent, or Firm—Milton L. Honig

(57) ABSTRACT

A packaged skin product is provided which includes at least one regular or irregular polygonal shaped patch for adhesive application to the skin. An outer carton formed of a series of walls functions as a receptacle for storing the patches. A front wall of the outer carton includes a window of a size and shape identical to one of the patches. A plurality of these patches adhere to a single backing sheet which is enclosed within a sealed laminated pouch. The window serves to inform a potential customer as to the size and visual nature of the enclosed patches.

11 Claims, 1 Drawing Sheet

PACKAGED SKIN PRODUCT

BACKGROUND OF THE INVENTION

1. Field of the Invention

The invention concerns a packaged skin product which includes an adhesive dermal patch packaged within an outer container providing potential customers an accurate representation of the enclosed patch.

2. The Related Art

Dermal patches have been available to the public for a number of years. These devices deliver chemicals to the skin for improving its condition.

Illustrative of the art is U.S. Pat. No. 5,785,978 (Porter et al.) which describes use of transdermal delivery devices known colloquially as patches adhering to the skin of an individual. These allow for sustained release of an active ingredient. The devices are said to be useful for improving the appearance of aging or photodamaged skin. Alpha-hydroxyacids and vitamins such as Vitamin C are suggested as suitable actives. A variety of shapes to fit various areas of the face are illustrated in the drawings.

WO 97/48387 (Fotinos) assigned to Lavipharm Corporation discloses use of pressure-sensitive adhesive patches in the treatment of acne. The Examples describe the patches as multi-layer laminates of circular shape (size of 1 $cm^2$) formed as a siliconized polyester film coated with an acrylate adhesive containing active ingredient. A film of polyethylene serves as a backing. The resultant circular dots spacedly disposed on the backing layer are then further packaged in a laminated sealed pouch. Several of these pouches are then packaged within a carton. These patches are available under the trademark Vichy. They are advertised for the treatment of pimples and blemishes. Ordinarily the patches number from 2 to 12 units attached onto a peelable backing sheet.

Potential customers have no way of knowing the physical nature of the product prior to purchase. Encasement by pouch and then outer carton hides the patches from view. It would be advantageous to educate customers about the product form prior to the purchase.

Accordingly it is an object of the present invention to provide a skin treatment product packaged to deliver dermal patches held within an outer container permitting the potential customer to visualize the patch.

SUMMARY OF THE INVENTION

A packaged skin product is provided which includes:
 (i) at least one regular or irregular polygonal shaped patch for adhesive application to the skin; and
 (ii) an outer carton being formed of a plurality of walls for containing the at least one polygonal shaped patch in a manner preventing viewing of the patch from outside the walls, and one of the walls including a window of a size and shape identical to one of the patches.

Ordinarily patches of this invention will include a plastic layer and an adhesive layer. A backing sheet is used as a support onto which the patches adhere. Advantageously about 4 to about 30 patches are adhesively positioned on a single backing sheet. More preferably about 6 to about 12 patches are placed per single backing sheet. Each of these sheets may then be enclosed within a sealed pouch. Typically the pouches are of laminate construction and heat sealed to exclude moisture.

Patches of this invention may contain cosmetic skin treatment actives formulated within the adhesive layer. Acrylic hydrogels are the most preferred form of adhesive.

Windows and patches of this invention preferably are of a round configuration. Alternative shapes are not excluded and may be rectangular, square, star-shaped, semicircular, rectangular or of non-regular borders.

In a first embodiment, an at least translucent plastic strip is held against an inner surface of the one wall and covers the window. Plastic strip and patch preferably have about an equivalent light transmission. Equivalence of light transmission and shape allows a potential purchaser to visualize the patch without the necessity of exposing it to atmospheric moisture. Information can be placed on an outer surface of the one wall, especially directly below the window, advising purchasers that the window represents the actual size of the patch. These windows and patches will normally range from about 0.5 to about 10 cm, preferably from about 0.8 to about 3 cm, more preferably from about 1 to about 2 cm, optimally about 1.5 cm. Light transmittance of the patches are very close to transparent but visually have a matte finish appearance.

BRIEF DESCRIPTION OF THE DRAWINGS

Further advantages, objects and features of the present invention will become more readily apparent from consideration of the following drawing in which.

DETAILED DESCRIPTION OF THE INVENTION

Now it has been found that potential customers can be educated as to the actual size and nature of patches concealed within a packaged skin product. Efficacy of the patches are maintained by enclosing them in a sealed environment which by its nature obscures them from view.

Figure 1:
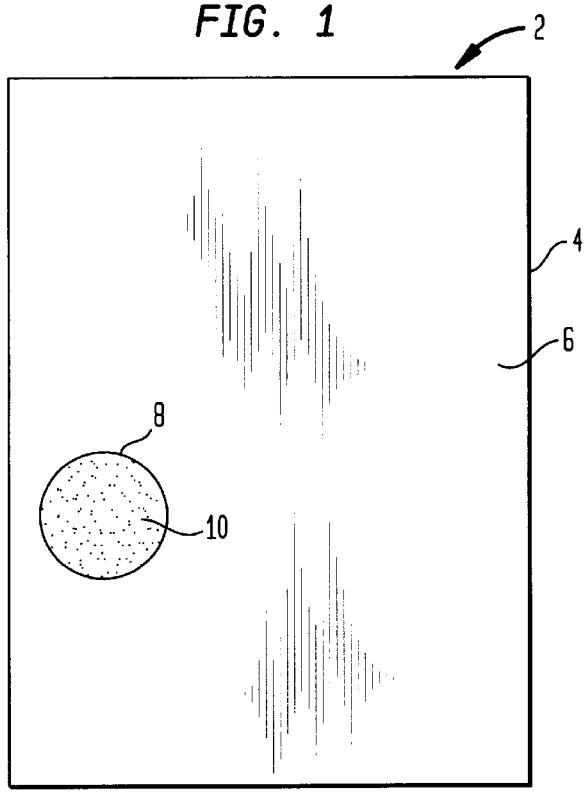
FIG. 1 is a front elevational view of one embodiment of the outer carton according to the present invention.

FIG. 1 illustrates the packaged product 2 which is constituted of an outer carton 4 formed from paperboard walls 6. On a front face of the outer carton is a window 8 traversing the front wall. A plastic strip 10 is held against an inner surface of the front wall and positioned across the window.

Figure 2:
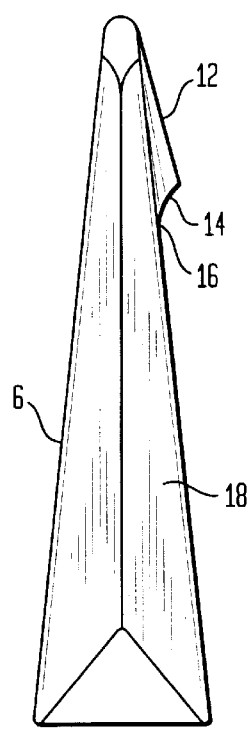
FIG. 2 is a side elevational view of the outer carton illustrated in FIG. 1.

FIG. 2 provides a side view of the packaged product. This view best illustrates a closure flap 12 having a tab 14 fitting within a slot 16 of a rear wall. Sidewalls of the outer package 4 are triangulated with a set of three panels 18.

Figure 3:
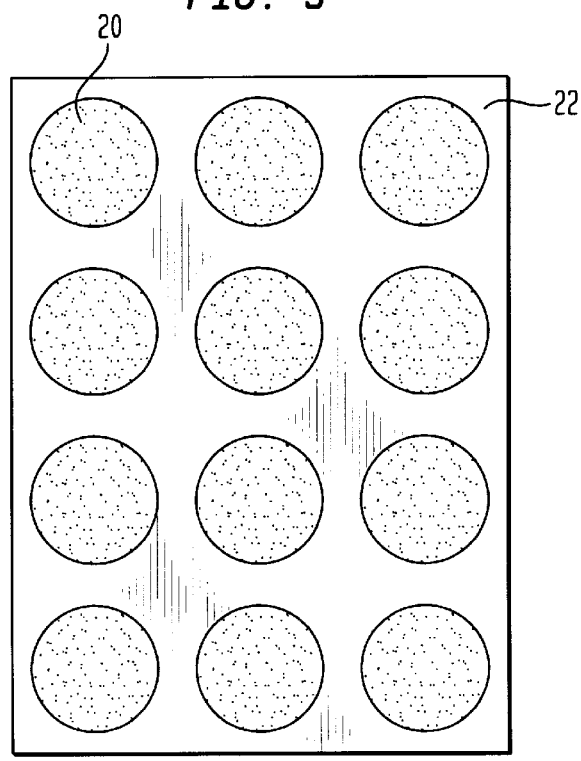
FIG. 3 is a backing sheet to which adhere a series of twelve round patches.

FIG. 3 illustrates a series of twelve patches 20 which may be formed of polyolefin, polyvinylacetate, polyethyleneterephthalate, polyvinylchloride or other plastic film. An adhesive layer, particularly an acrylic hydrogel, is deposited on one side of a plastic layer forming the patch. The adhesive layer allows the patch to adhere to a backing sheet 22 from which the patches are peelable. The backing sheet with adhering patches (known as dots) are then sealably enclosed within a pouch. The pouch consists of two laminate plastic foils heat sealed along the periphery of the foils.

Polyacrylates are the preferred adhesives for use with patches of the present invention. Construction of such patches are well known in the art and disclosed in U.S. Pat. No. 5,306,503 and U.S. Pat. No. 5,458,885, both assigned to LTS Lohmann Therapie-Systeme of Germany. A variety of skin effective actives may be included within the adhesive.

Among the actives are salicylic acid, alpha-hydroxycarboxylic acids, retinoids (e.g. retinol and retinoic acid), bisabolol, glycyrrhetinate, triclosan, Vitamin C and combinations thereof.

Advantageously the plastic strip 10 and patch will not only be of identical size but each will have a generally similar light transmission. In this manner, a potential customer can appreciate both the shape and also the "look" of the patch or dot. Ordinarily the "look" will be that of a matte finish. An area on wall 6 below the window may carry a line of instruction such as "Actual Size of Dot" to reinforce the meaning behind the window.

Except in the operating and comparative examples, or where otherwise explicitly indicated, all numbers in this description indicating amounts of material ought to be understood as modified by the word "about".

What is claimed is:

1. A packaged skin product comprising:
   (i) at least one regular or irregular polygonal shaped patch for adhesive application to the skin, the at least one patch being enclosed within a sealed pouch obscuring the patch from view and the patch comprising a cosmetic skin active; and
   (ii) an outer carton being formed of a plurality of walls for containing the pouch enclosing the at least one polygonal shaped patch in a manner preventing viewing of the patch from outside the walls, and one of the walls including a window of a size and shape identical to one of the patches.

2. The product according to claim 1 wherein the at least one patch comprises a plastic layer and an adhesive layer, the patch adhering to a backing sheet.

3. The product according to claim 2 wherein the cosmetic skin active is formulated within the adhesive layer.

4. The product according to claim 1 wherein from about 4 to about 30 patches adhere to a single backing sheet.

5. The product according to claim 4 wherein from about 6 to about 12 patches adhere to a single backing sheet.

6. The product according to claim 3 wherein the adhesive layer is an acrylic hydrogel.

7. The product according to claim 1 wherein the window and the at least one patch are round.

8. The product according to claim 1 further comprising an at least translucent plastic strip held against an inner surface of the one wall and covering the window.

9. The product according to claim 8 wherein light transmission across the plastic strip and the patch are equivalent.

10. The product according to claim 1 wherein the window has a matte finish similar to the finish of the patch.

11. The product according to claim 1 wherein the outer carton has sidewalls triangulated with a set of three panels.

* * * * *